United States Patent [19]

Ender et al.

[11] Patent Number: 4,502,491
[45] Date of Patent: Mar. 5, 1985

[54] APPARATUS FOR DETERMINING THE PRESSURE BETWEEN A SUPPORT DRESSING AND A BODY PORTION SURROUNDED BY SAID SUPPORT DRESSING

[75] Inventors: Hans G. Ender, Ferstelgasse 6/20, A-1090 Vienna, Austria; Wilhelm Sillaba, Vienna, Austria

[73] Assignee: Hans G. Ender, Vienna, Austria

[21] Appl. No.: 360,465

[22] Filed: Mar. 22, 1982

[51] Int. Cl.³ .............................................. A61B 5/10
[52] U.S. Cl. ................................. 128/782; 128/748; 128/678; 73/731; 116/270
[58] Field of Search ............... 128/678, 694, 748, 774, 128/782; 73/730, 731; 116/270, 272

[56] References Cited

U.S. PATENT DOCUMENTS 4,286,603 9/1981 Marshall ............................... 128/782
4,365,638 12/1982 Leveque et al. ..................... 128/774

Primary Examiner—Henry J. Recla
Assistant Examiner—Karin M. Reichle
Attorney, Agent, or Firm—Holman & Stern

[57] ABSTRACT

An apparatus for determining the pressure between a support dressing and a body portion surrounded by said support dressing comprises a device for sensing the pressure, a device for indicating the pressure sensed and an arrangement transferring the pressure sensed to the device for indicating the pressure. The device for sensing the pressure may have a first part borne by the support dressing and a second part movable relative to the first one and being urged against the body portion by a spring or the like, the second part being connected to an indicator cooperating with a graduation through a lever system. The device for sensing the pressure may, however, also comprise a cavity filled with an incompressible fluid, said cavity being defined by a wall which is flexible at least in a region abutting the body portion. The cavity is connected via a conduit system with a sight glass cooperating with a scale, or a hollow body enclosing the cavity acts on a displaceable part connected by a lever system to an indicator cooperating with a graduation.

18 Claims, 7 Drawing Figures

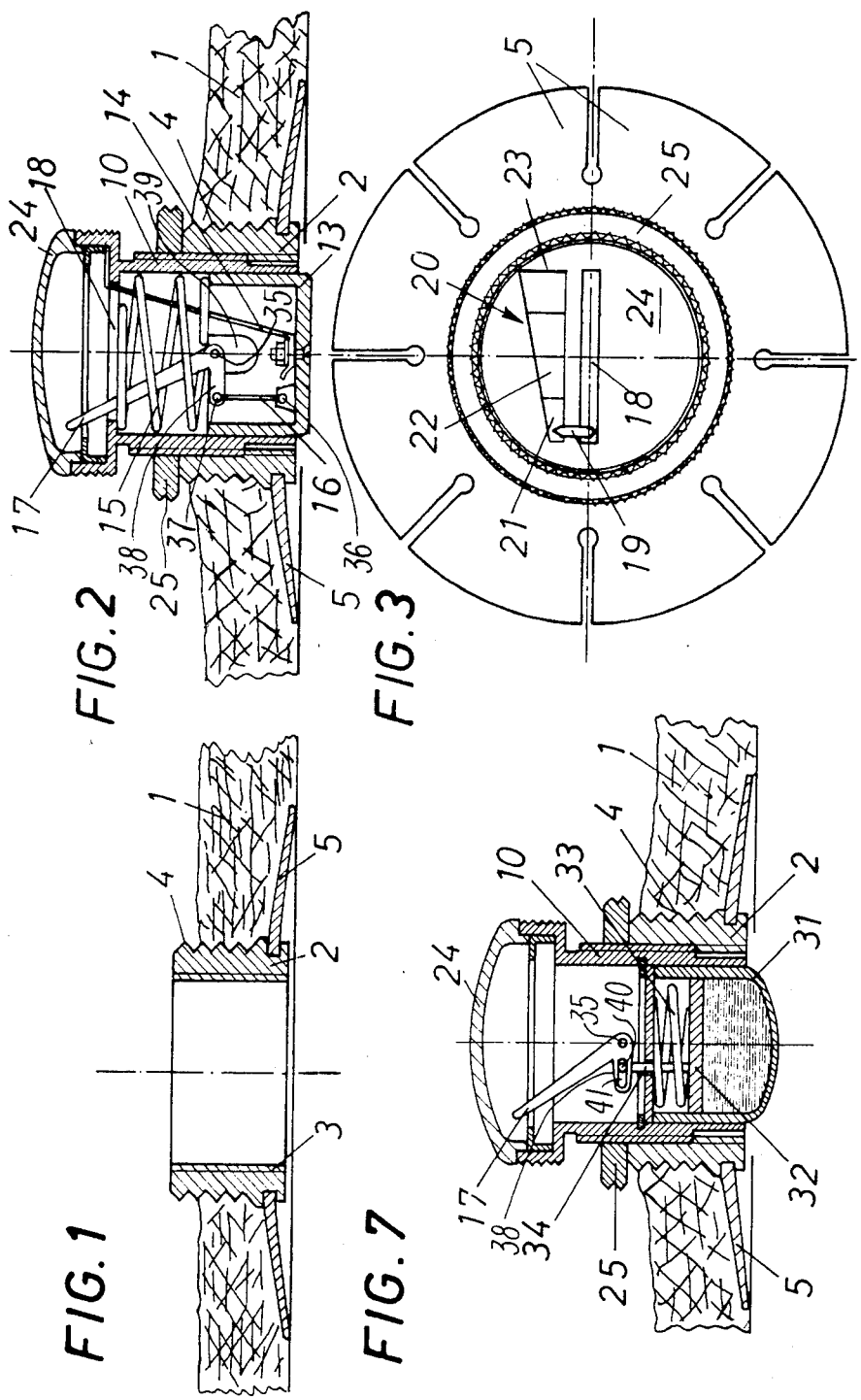

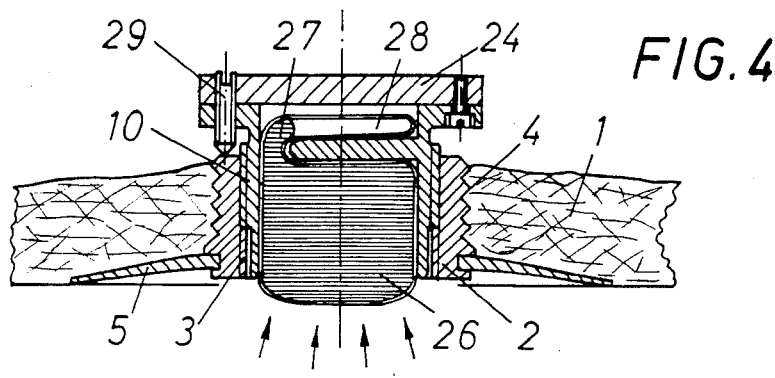
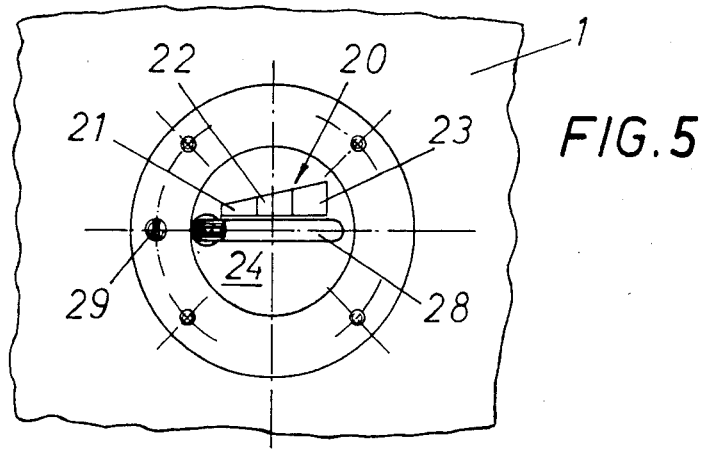
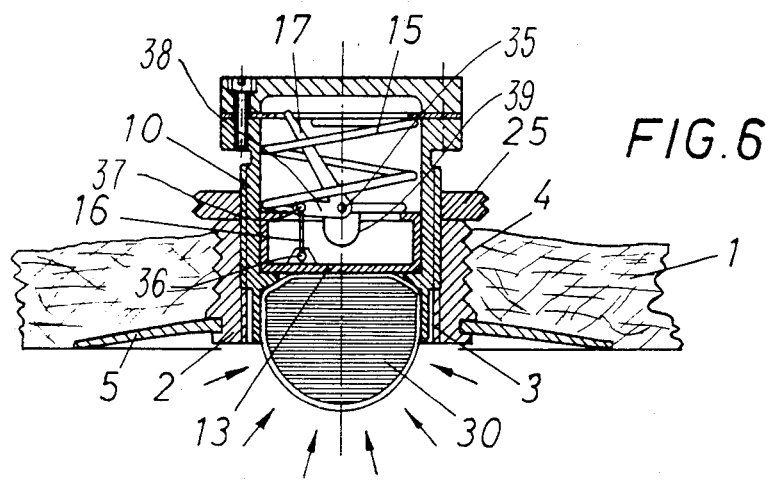

APPARATUS FOR DETERMINING THE PRESSURE BETWEEN A SUPPORT DRESSING AND A BODY PORTION SURROUNDED BY SAID SUPPORT DRESSING

BACKGROUND OF THE INVENTION

1. Field of the Invention

The present invention relates to an apparatus for determining the pressure between a support dressing and a body portion surrounded by said support dressing.

2. Description of the Prior Art

With certain kinds of physical injuries, such as fractures, strains or the like, the body portion concerned is surrounded by a support dressing in order to provide a splinting, to maintain motionless this body portion and to ensure the recovery of the fracture in the correct position of the fragments at the point of the fracture. Generally, a plaster of Paris dressing or another rigid dressing producing a suitable splinting of the body portion concerned is used as a support dressing. It is a disadvantage of this procedure that normally this body portion swells up within a short time after application of the support dressing, whereby the swelling can be to such an extent that the related limb is tied off so strongly by the inflexible support dressing that an irreversible derangement and in extreme cases even a mortification of said limb may result.

In order to avoid this drawback it is known to split the support dressing in the first instance and to bend it up when the swelling occurs so that the swollen limb has space within the support dressing, and only to apply a closed plaster of Paris dressing after termination of the swelling. By splitting such a plaster of Paris dressing the disadvantage is produced that the body portion concerned is insufficiently supported, in particular when the swelling does not occur to the extent expected or when it fades away early. Then, the fragments can displace themselves at the point of fracture and the desired curing of the fracture is no longer ensured.

SUMMARY OF THE INVENTION

It is an object of the invention to provide an apparatus by which a continuous surveillance of the course of the pressure is made possible either by the patient himself or by a supervisor. Thereby an increase of the pressure should be recognized so early that there remains enough time to visit a doctor or a hospital.

It is a further object of the invention to provide a small sized apparatus to be accommodated in the support dressing. The apparatus according to the invention will make it possible not only to determine an intolerable increase of pressure, but also a decrease of the pressure below a predetermined value, since in this case a sufficient support of the body portion is no longer accomplished. Moreover, the apparatus according to the invention will enable an adjustment so that starting from a basic value positioned by the adjustment, an increase or a decrease of the pressure as well as the relative amount of these values in relation to the adjusted basic value may be determined in a simple manner.

Finally, it is an object of the present invention to construct the apparatus in such a manner that the essential components of the apparatus could be removed when a surveillance of the pressure is no longer necessary, and could be applied to another patient without thereby damaging the support dressing.

BRIEF DESCRIPTION OF THE DRAWINGS

Preferred embodiments of the invention are schematically illustrated in the accompanying drawings wherein FIG. 1 is a longitudinal cross-sectional view of a retaining body of an apparatus according to the invention anchored in a support dressing;

FIG. 2 is a cross-sectional view of an embodiment of an apparatus according to the invention anchored in a support dressing;

FIG. 3 is a top plan view of FIG. 2 wherein the support dressing is omitted;

FIG. 4 is a longitudinal cross-sectional view of a further embodiment of an apparatus according to the invention anchored in a support dressing;

FIG. 5 is a top plan view of FIG. 4; and

FIGS. 6 and 7 are cross-sectional views showing further embodiments of the apparatus according to the invention.

DESCRIPTION OF THE PREFERRED EMBODIMENTS

In a support dressing 1, for instance being a plaster of Paris dressing or another rigid dressing, a retaining body 2 is anchored and is formed as a socket. The socket is provided with an internal thread 3 and has projections on its periphery. These projections may be formed by flute-defining peaks 4. Instead of these flute-defining peaks 4, or additionally to the same, flukes 5, for instance of plastic material, may be mounted at the lower end of the retaining body, thus likewise forming projections. The flute-defining peaks 4 as well as the flukes 5 ensure a secure and immovable anchoring of the retaining body 2 within the support dressing 1 when the latter has solidified. The flukes 5 bearing the retaining body 2 prop against the body portion during the application of the support dressing so that the retaining body 2 takes the desired position.

Into the internal thread 3 of the retaining body 2 either the external thread of a temporary filling body (not shown) or the external thread of a housing 10 may be screwed, the latter containing means for sensing the pressure, means for indicating the pressure sensed and an arrangement through which the pressure sensed is transfered to said means for indicating this pressure. This design makes it possible, first only to anchor the retaining body 2 in the support dressing. The opening within the retaining body 2, wherein the housing 10 is then screwed, is suitably closed by the temporary filling body during this procedure. In this way the penetrating of liquid plaster or the like into the interior of the retaining body 2 is prevented. When the support dressing has solidified, the filling body is screwed out and the housing 10 is inserted. By screwing the housing more or less deep into the retaining body 2 an adjustment of the apparatus for indicating the pressure sensed may be effected. Furthermore, this arrangement has the advantage that the housing 10 may be screwed out of the retaining body 2 after the swelling has been reduced, and may be applied anew for another patient without damaging the support dressing 1 when removing the housing 10. Then, only the retaining body 2 remains in the support dressing 1 whereby the opening may be closed again by the filling body.

The internal thread 3 of the retaining body 2 and the external thread of the housing 10 cooperating with it suitably are formed as a fine thread, thus facilitating the adjustment.

The filling body should extend up to the lower end of the retaining body 2 so that the thread 3 is protected over its whole length and after removal of the housing 10 an oedema may not be caused by the cavity thus formed.

The adjusted position of the housing 10 within the retaining body 2 is secured in the manner described below in detail so that an undesired misadjustment of the housing 10 is not possible.

The means for sensing the pressure of the apparatus according to the invention as shown in FIGS. 2 and 3 comprises an insert element 13 slidably arranged within the housing 10 which is secured against dropping out by a yarn 14 or the like and which is resiliently urged into its inoperative position by a spring 15. The insert element 13 is connected to an indicating device, such as a needle 17 pivotally mounted at one end to the housing 10 by pivot pin 35, by a lever 16 pivotally connected at its ends by pivot pins 36, 37 to insert element 13 and an arm 38 extending at an angle from the pivot end of needle 17, the indicating needle 17 being passed through a slot 18 in the front wall of the housing 10 and being bent to form an indicator 19 at its end protruding from the slot 18. This indicator 19 cooperates with a graduation 20 applied to the outer surface of the front wall of the housing 10. Slot 39 is provided in element 13 to accommodate pivot pin 35. This graduation 20 is divided into three ranges 21, 22 and 23. In this connection the arrangement may be such that for instance, when the indicator 19 is within the range 21, there is a too low pressure between the support dressing and the body portion, when the indicator 19 is positioned within the range 22 it indicates the pressure desired, and when the indicator 19 reaches the range 23, there is a pressure requiring a medical intervention. The arrangement, however, may also be such that the range 21 corresponds to the normal pressure and the range 22 limits a pressure of tolerable values, whereas the range 23 defines the critical range wherein the doctor has to take precautionary measures. In each case the housing has to be screwed so deeply into the retaining body 2 that with normal pressures the indicator is positioned about the center of that range defining the normal pressure.

Afterwards, the position of the housing 10 is secured in accordance with the FIGS. 2 and 3 by a lock nut 25 so that the housing 10 can no longer be twisted.

The indicator 19 and the graduation 20 are covered by a glass 24 formed as a magnifying lens so that the pressure values represented are clearly distinguishable although the dimensions of the apparatus are small.

In the embodiment according to the FIGS. 4 and 5 the means for sensing the pressure comprise a hollow body 26 located within the housing 10, having flexible walls and protruding from the lower side of the housing, thus abutting against the body portion. The hollow body 26 is filled with an incompressible fluid and is connected through a conduit 27 with a sight glass 28 wherein the end of the head of liquid is visible. The sight glass 28 likewise cooperates with a graduation 20 similarly having the three above-mentioned ranges 21 to 23. By the pressure occurring with a swelling of the body portion and acting in the direction of the arrows onto the hollow body 26 having flexible walls, the head of liquid within the sight glass 28 is displaced, whereby the change of pressure is visible on the graduation 20.

Also with the apparatus shown in FIGS. 4 and 5 an adjustment may be effected in that the housing 10 is screwed into the retaining body 2 so deeply that the end of the head of liquid is just at the center of that range of the graduation 20 which is limited by those values between which the pressure may vary without affecting the patient. The adjusted position of the housing 10 is secured in the embodiment according to FIGS. 4 and 5 by a set screw 29 screwed in the housing 10 at the front wall and cooperating with the front wall of the retaining body 2, rather than by a lock nut.

In the embodiment according to FIGS. 2 and 3, it may occur that when the pressure does not act in the sliding direction of the insert element 13, the latter may become jammed, thus indicating incorrect pressure values. In order to avoid this, the insert element 13 in conformity with the embodiment of FIG. 6 is biased via a hollow body 30 having flexible walls. An incompressible fluid is provided in the hollow body. That area of the wall of the hollow body which abuts against the body portion is curved. This embodiment ensures that pressures acting onto the hollow body 30 from different directions are transfered in the sliding direction onto the insert element 13, thus preventing a jamming of the latter.

In a hollow body 31 of the embodiment according to FIG. 7 which abuts with a flexible wall against the body portion, a piston 32 is provided being biased on one side by a fluid within the hollow body 31 and on the other side by a spring 33. A piston rod 34 passing through an opening in the end plate of the hollow body 31 is pivotally connected at its end 40 in slot 41 in arm 38 of indicating needle 17 passed through the slot 18 in the front wall of the housing and being bent to form an indicator 19 at its end projecting from this slot, just as in the embodiment of FIGS. 2 and 3. The indicator 19 again cooperates with a graduation 20 covered by a glass 24 formed as a magnifying lens.

The position of the housing 10 in relation to the retaining body 2 in this embodiment is ensured again by a lock nut 25, but, of course, instead of the lock nut 25, a set screw 29 may be provided.

What we claim is:

1. An apparatus for determining the pressure between a support dressing which has been applied to a part of a persons body and that portion of the body surrounded by said support dressing comprising:

tubular socket retaining body means having first and second ends and adapted to extend through said support dressing, said retaining body means including means for immovably anchoring said retaining body means in said support dressing with said first end adjacent the interior of said support dressing;

an internal fastening means in said tubular socket;

removable means for sensing the pressure extending through said retaining body means including a first housing part having an external fastening means thereon removably mounted in said retaining body means in fixed relationship to said support dressing with said internal and external fastening means cooperatively engaged, at least one separate second part mounted in and movable relative to said first part in response to said pressure, said at least one separate second part extending from said first part beyond said first end of said retaining body means, and means adapted to urge said at least one movable second part against said body portion;

means for indicating the pressure sensed by said sensing means; and means operatively associated with said at least one movable second part and said indicating means for actuating said indicating means.

2. An apparatus as claimed in claim 1 wherein said at least one second part comprises:
wall means defining a cavity;
an incompressible fluid in said cavity; and
said wall means having an area adapted to be in abutting relationship against said body portion and being flexible at least in said area.

3. Apparatus as claimed in claim 2, wherein said indicating means comprise
a sight glass connected with said cavity so that said fluid can flow into said sight glass, and scale means cooperatively arranged within the range of said sight glass for indicating the pressure between said support dressing and said body portion.

4. Apparatus as claimed in claim 3, wherein said scale means is divided into three ranges.

5. Apparatus as claimed in claim 3, further comprising magnifying lens means for covering said scale means.

6. Apparatus as claimed in claim 2 and further comprising,
a movable surface means abutting against at least a portion of said wall means, and
lever means connected between said surface means and said indicating means for actuating said indicating means.

7. Apparatus as claimed in claim 2 further comprising,
piston means in said cavity biased by said fluid, and
piston rod means connected between said piston means and said indicating means for actuating said indicating means.

8. Apparatus as claimed in claim 2, wherein said area of said wall means adapted to be in abutting relationship against said body portion, is curved.

9. An apparatus for determining the pressure between a support dressing which has been applied to a part of a persons body and that portion of the body surrounded by said support dressing comprising:
retaining body means having first and second ends and adapted to be anchored immovably in said support dressing with said first end adjacent the interior of said support dressing;
means for sensing the pressure including a first part removably mounted in said retaining body means and adapted to be in fixed relationship to said support dressing, and a second part slidably mounted in said first part and movable relative to said first part in response to said pressure, said second part also extending from said retaining body means beyond said first end;
biasing means adapted to urge said movable second part against said body portion;
means for indicating the pressure sensed by said sensing means; and
lever means connected between said movable second part and said indicating means for actuating said indicating means.

10. Apparatus as claimed in claim 9, wherein said retaining body means comprises a tubular socket provided at least partially with an internal screw thread, and said first part comprises a cylindrical housing means having an external screw thread adapted to be screwed into said internal screw thread.

11. Apparatus as claimed in claim 10, and further comprising lock nut means screwed onto said housing means for securing the position thereof in relation to said tubular socket.

12. Apparatus as claimed in claim 9 or 2, wherein said sensing means and said indicating means are housed in said first part.

13. Apparatus as claimed in claim 12, further comprising locking screw means for securing said first part in said retaining body means.

14. Apparatus as claimed in claim 9 or 2, wherein said retaining body means has projection means protruding from its periphery for movably anchoring the retaining body means in said support dressing.

15. Apparatus as claimed in claim 9 or 2, further comprising a filling body adapted for insertion into said retaining body means when said sensing means is removed therefrom.

16. Apparatus as claimed in claim 9 or 6, wherein said indicating means comprises,
pointer means operatively connected with said lever means, and
scale means cooperatively disposed within the range of said pointer means for indicating the pressure between said support dressing and said body portion.

17. Apparatus as claimed in claim 16, wherein said scale means is divided into three ranges.

18. Apparatus as claimed in claim 16 and further comprising magnifying lens means for covering said scale means.

* * * * *